US 6,548,716 B1

(12) United States Patent
Lange

(10) Patent No.: US 6,548,716 B1
(45) Date of Patent: Apr. 15, 2003

(54) PROCESS FOR PREPARING A 1,3-DIOL

(75) Inventor: Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/239,083

(22) PCT Filed: Mar. 22, 2001

(86) PCT No.: PCT/EP01/03277

§ 371 (c)(1),
(2), (4) Date: Sep. 18, 2002

(87) PCT Pub. No.: WO01/70658

PCT Pub. Date: Sep. 27, 2001

(30) Foreign Application Priority Data

Mar. 22, 2000 (EP) .............................. 00302362

(51) Int. Cl.$^7$ .................. C07C 27/04; C07C 29/14; C07C 31/18; C07C 27/00; C07C 29/00
(52) U.S. Cl. .................. 568/862; 568/852; 568/861
(58) Field of Search ............... 568/862, 861, 568/852

(56) References Cited

U.S. PATENT DOCUMENTS

| | | | |
|---|---|---|---|
| 5,096,688 A | 3/1992 | Miller et al. | |
| 5,364,984 A | 11/1994 | Arntz et al. | |
| 5,463,144 A | 10/1995 | Powell et al. | |
| 5,463,145 A | 10/1995 | Powell et al. | |
| 5,463,146 A | 10/1995 | Slaugh et al. | |
| 5,527,973 A | 6/1996 | Kelsey | |
| 5,545,765 A | 8/1996 | Slaugh et al. | |
| 5,545,766 A | 8/1996 | Powell et al. | |
| 5,545,767 A | 8/1996 | Weider et al. | |
| 5,563,302 A | 10/1996 | Weider et al. | |
| 5,576,471 A | 11/1996 | Semple et al. | |
| 5,585,528 A | 12/1996 | Powell et al. | |
| 5,684,214 A | 11/1997 | Weider et al. | |
| 5,723,389 A | 3/1998 | Slaugh et al. | |
| 5,770,776 A | 6/1998 | Powell et al. | |
| 5,786,524 A | 7/1998 | Powell et al. | |
| 5,841,003 A | 11/1998 | Slaugh et al. | |
| 5,945,570 A | 8/1999 | Arhancet et al. | |
| 5,986,145 A | 11/1999 | Powell et al. | |

FOREIGN PATENT DOCUMENTS

| | | | |
|---|---|---|---|
| EP | 0 478 850 B1 | 9/1994 | ........... C07C/45/58 |
| WO | 94 18154 A | 8/1994 | ........... C07C/67/38 |
| WO | 97 38964 A | 10/1997 | ........... C07C/67/38 |
| WO | 98 57913 | 12/1998 | ......... C07C/29/141 |

OTHER PUBLICATIONS

New Syntheses with Carbon Monoxide (Springer–Verlag, 1980) pp. 131–132.

*Primary Examiner*—Samuel Barts
*Assistant Examiner*—Elvis O. Price

(57) ABSTRACT

A process for preparing a 1,3-diol by hydrogenating a feed having a 3-hydroxyaldehyde in the presence of a catalyst and a hydrogen source, wherein syngas is used as hydrogen source, and the catalyst is a heterogeneous catalyst having copper on a support.

17 Claims, No Drawings

PROCESS FOR PREPARING A 1,3-DIOL

This application is a 371 of PCT/EP01/03277, filed Mar. 22, 2001.

FIELD OF THE INVENTION

The present invention relates to a process for preparing a 1,3-diol by hydrogenating a feed comprising a 3-hydroxyaldehyde in the presence of a catalyst and a hydrogen source, wherein syngas is used as hydrogen source, and the catalyst is a heterogeneous catalyst comprising copper on a support.

BACKGROUND OF THE INVENTION 1,3-Diols have plenty of uses, particularly in the synthesis of polymers. For instance, CORTERRA® polymer is a polyester made of 1,3-propanediol (PDO) and terephthalic acid, which polymer has outstanding properties. Substituted versions of PDO may find similar use. Commercially attractive routes to prepare such 1,3-diols are therefore highly desirable.

One of the more important routes for preparing 1,3-diols involves the hydroformylation of an oxirane, followed by the hydrogenation of the intermediate 3-hydroxyaldehyde. An alternative process involves the hydration of acrolein or higher homologue, again followed by the hydrogenation of the resulting 3-hydroxyaldehyde.

The hydroformylation of oxiranes (epoxides) is described in "New Synthesis with Carbon Monoxide" (Springer-Verlag, 1980), pp. 131–132, and in various patents in the name of Shell (hydroformylation processes have, for instance, been described in EP-A-0478850; and in U.S. Pat. No. 5,463,144; U.S. Pat. No. 5,463,145; U.S. Pat. No. 5,463,146; U.S. Pat. No. 5,527,973; U.S. Pat. No. 5,545,765; U.S. Pat. No. 5,545,766; U.S. Pat. No. 5,545,767; U.S. Pat. No. 5,563,302; U.S. Pat. No. 5,576,471; U.S. Pat. No. 5,585,528; U.S. Pat. No. 5,684,214; U.S. Pat. No. 5,723,389; U.S. Pat. No. 5,770,776; U.S. Pat. No. 5,786,524; U.S. Pat. No. 5,841,003; U.S. Pat. No. 5,945,570; and U.S. Pat. No. 5,986,145).

The conversion of the 3-hydroxyaldehyde is typically carried out by hydrogenation thereof with hydrogen gas in the presence of a homogeneous or heterogeneous catalyst. For instance, hydrogenation of 3-hydroxypropanal (HPA) into 1,3-propanediol (PDO) in the presence of a heterogeneous catalyst is disclosed in WO-A-98/57913 and the prior art described in this reference. This reference also describes the important criteria of a suitable catalyst: high activity and selectivity with a small volume of catalyst, long operational service life, and reasonably priced.

However, many such catalysts lack selectivity and/or stability in slightly acidic environments, and/or in the presence of carbon monoxide. Therefore, a potentially attractive hydrogen source in the form of synthesis gas ("syngas", a blend of $H_2$ and CO) is not used. The present invention aims to provide catalysts that may be used in the preparation of a 1,3-diol by hydrogenation of a 3-hydroxyaldehyde in the presence of syngas as hydrogen source.

As mentioned, 1,3-diols may be the product of a multistep process, wherein syngas is used in a step prior to the hydrogenation, i.e., in the hydroformylation step.

In such processes a catalyst capable of hydrogenating the product of the preceding hydroformylation step in the presence of syngas would be particularly attractive.

It was therefore an aim to provide a process for preparing a 1,3-diol by hydrogenating a feed comprising a 3-hydroxyaldehyde in the presence of a catalyst and a hydrogen source, wherein the catalyst is capable of handling syngas as hydrogen source, and wherein the catalyst meets the aforementioned important criteria.

SUMMARY OF THE INVENTION

Accordingly, the present invention provides a process for preparing a 1,3-diol by hydrogenating a feed comprising a 3-hydroxyaldehyde in the presence of a catalyst and a hydrogen source, wherein syngas is used as hydrogen source, and the catalyst is a heterogeneous catalyst comprising copper on a support.

The feed to the process of the present invention preferably comprises the product of an oxirane hydroformylation step, which product comprises a 3-hydroxyaldehyde, a solvent and a homogeneous hydroformylation catalyst. Said homogeneous hydroformylation catalyst preferably comprises a Co-based and/or Rh-based hydroformylation catalyst.

More preferably, a) the oxirane is hydroformylated by reaction with syngas in the presence of a homogeneous hydroformylation catalyst and a solvent, forming a 3-hydroxyaldehyde feed, and (b) the 3-hydroxyaldehyde feed is hydrogenated in the presence of a catalyst comprising copper on a support and syngas as hydrogen source. Preferably, hydroformylation step 1) and hydrogenation step b) are carried out sequentially in connected reactor vessels or in a single reactor vessel.

More preferably, the hydroformylation step a) and the hydrogenation step b) are carried out simultaneously in a single reactor vessel.

The process of the present invention comprises the hydrogenation of feed comprising a 3-hydroxyaldehyde, i.e. a compound of the general formula

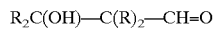

wherein each R independently may be a hydrogen atom or may (jointly) be a hydrocarbon group that is substituted or unsubstituted, and/or aliphatic or aromatic. Each group R may independently vary in size, for instance, from 1 to 20 carbon atoms, preferably from 1 to 10 carbon atoms. In addition, they may bear one or more substituents selected from hydroxy, alkoxy, carbonyl, carboxy, amino, cyano, cyanato, mercapto, phosphino, phosphonyl, and/or silyl groups, and/or one or more halogen atoms. The preferred 3-hydroxyaldehydes are those having in total from 3 to 12 carbon atoms, more preferably from 3 to 8 carbon atoms. The most preferred 3-hydroxyaldehyde is HPA, i.e. wherein each R is a hydrogen atom.

Synthesis gas is a blend of hydrogen and carbon monoxide. It typically is made by partial combustion of a petroleum feed. Commercial syngas comprises hydrogen and carbon monoxide in an $H_2/CO$ ratio of about 1.0–2.0. Syngas with a higher $H_2/CO$ ratio, e.g., up to about 10.0, and higher, may be prepared by the so-called water gas shift reaction, and such gases may also be used in the process of the present invention. On the other hand, it is an advantage of the present invention that it may cope with carbon monoxide-rich gases, at $H_2/CO$ ratios as low as about 0.5. The preferred $H_2/CO$ ratio hence varies from about 0.5 to about 10.0, more preferably from about 1.0 to about 5.0.

As indicated, the catalyst comprises copper on a support, which is believed to be at least partially in a metallic state under operating conditions. The catalyst may be a sophisticated catalyst wherein the copper is part of an alloy, and/or wherein the catalyst comprises additional promoter metals. Suitable alloys include metals of Groups 8 to 11 of the Periodic Table. Suitable promoter metals include metals of Groups 1 to 7. However, ordinary catalysts, based on copper as the only active component, have been founds to be quite acceptable.

The nature of the catalyst support is not essential. Suitable supports include inert carriers composed of a clay, a metallic or glass sponge, or based on an inorganic carbide, or oxide, or carbon. For instance, the support may be based on oxides of Group 2–6 and 12–14 metals and mixtures thereof, e.g. ZnO, titania, alumina, zirconia, silica and/or zeolites. Preferred supports are resistant to an acidic medium. Suitable results have been achieved with copper on ZnO, on silica, and on $Cr_2O_3$.

The support may be used as fine powder or shaped into mouldings such as, for example, pellets, granules, or extrudates using methods known in the art, such as those described in U.S. Pat. No. 5,364,984. Alternatively, the support may be in the shape of a honeycomb, a foam, a sponge or similarly large monolith.

The amount of copper may also vary widely. For instance, the copper may be present on the support in a quantity of about 0.1 to about 80 w % (% by weight), preferably about 10 to about 50 w %, more preferably about 25 to about 35 w %, relative to the support (i.e., g Cu per 100 g of support).

The synthesis of the copper catalyst is conventional, typically involving the co-precipitation of copper and support precursor. Optionally it can also be prepared by doping a carrier with a copper solution, calcining the loaded carrier, and reducing the same at elevated temperatures under $H_2$. Various supported copper catalyst are commercially available, e.g., for use in the hydrogenation of esters to the corresponding alcohols. Copper containing catalysts are also described in U.S. Pat. No. 5,096,688, which is herein incorporated by reference, in a two-stage process for converting synthesis gas into higher alcohols. This document describes its use for the hydrogenation of undesirable non-alcohol oxygenates and the conversion of water and carbon monoxide in hydrogen gas and carbon monoxide.

The supported copper catalyst may bemused in a continuous process, a semi-continuous process of a batch process. The preferred manner is described in respect of the preferred embodiment disclosed hereinbelow.

The hydrogenation conditions are not very critical. Typically the carbonyl feed is hydrogenated at a temperature ranging from ambient to about 150° C., preferably from about 40 to about 80° C., and at a pressure ranging from atmospheric to about 15 Mpa (about 150 bar), preferably from about 4 to about 10 Mpa (about 40 to about 100 bar). In the case of continuous processes, liquid hourly space velocities of about 0.1 to about 10 10 h⁻1 are preferred. In batch processes, reaction times varying from about 0.1 to about 10 hours are suitable. Finally, in batch processes, the catalyst may be used in any suitable amount, ranging from about 0.1 to about 50 w %, preferably from about 1.0 to about 10 w %, of catalyst calculated on the weight of the carbonyl compound.

The preferred embodiment comprises the hydrogenation of aqueous HPA solutions, for instance solutions made by the hydroformylation of ethylene oxide (EO) in the presence of a cobalt- or rhodium-based catalyst. In principal, any oxirane may be used, leading to the 3-hydroxyaldehyde mentioned above.

The process of the present invention is particularly beneficial in the multistep preparation of PDO from EO, which ordinarily involves the removal of the hydro-formylation catalyst prior to hydrogenation. Thus, it is known that many cobalt-based catalysts require the presence of carbon monoxide to remain in solution. Since in the "conventional" HPA hydrogenation process only hydrogen gas is present, any remaining catalyst precipitates and pollutes the reactor. In the process of the present invention, such hydroformylation catalysts need no longer be removed prior to the hydrogenation.

Surprisingly, it has been discovered that the copper supported catalyst can hydrogenate HPA with syngas, under conditions that completely poison conventional Group 8–10 metal hydrogenation catalyst. Furthermore, the copper-based catalyst may be present during the hydroformylation of the oxirane, thus substantially reducing the fixed equipment costs. In the most preferred embodiment, this would lead to a "single step" production of PDO (or similar 1,3-alkanediol) from EO (or corresponding oxirane).

The present invention is illustrated in respect of the hydrogenation of a 3-hydroxyaldehyde (HPA) under syngas, comparing the process of the present invention with that of the prior art using a ruthenium-based catalyst. The present invention is also illustrated in respect of a "single step" PDO process.

EXAMPLES

In the Examples the following hydrogenation catalysts have been used:

Cu/Zn a ZnO/alumina catalyst containing ~40 w % of Cu
Cu/Cr a chromite catalyst containing ~37 w % of Cu
Ag/Al an alumina catalyst containing ~14 w % of Ag
Au/Ti a titania catalyst containing ~2 w % Au
RU/foam an alpha-alumina foam of 40 pores per inch containing ~2 w % of Ru Prior to the reaction, the hydrogenation catalyst was reduced at 300° C. for 11 hours under 0.5 MPa (5 bar) $H_2$.

Experiment A

In a typical experiment, a 300 ml autoclave was loaded with various amounts of a hydrogenation catalyst. The autoclave was then filled with 150 ml of an aqueous solution containing ~21 w % HPA and operated batch-wise at 45° C. and 9 MPa (90 bar) $H_2$ or 9 MPa (90 bar) syngas (3:1 $H_2$:CO) for several hours.

Results and Discussion A

Two catalysts were investigated; Cu/Cr and Ru/foam. The results in Table 1 below clearly showed that the Ru-based catalyst was active under pure hydrogen but almost inactive under syngas. By contrast, the Cu/Cr catalyst showed a good activity under both pure hydrogen and syngas. It will be noticed that acetals can be formed by condensation of HPA with PDO.

TABLE 1

HPA hydrogenation under syngas

| exp. # | hydrogenation catalyst name | [g] | HPA [mmole] | time [h] | PDO | acetal | PDO + acetal |
|---|---|---|---|---|---|---|---|
|  |  |  |  |  | [mole per 100 mole HPA in feed] | | |
| Hydrogenation under 9 MPa (90 bar) $H_2$ (65° C.) | | | | | | | |
| 37 | Ru/foam | 49 | 206.00 | 0.75 | 21.0 | 5.0 | 26.1 |
|  |  |  |  | 1.5 | 37.1 | 5.1 | 42.2 |
|  |  |  |  | 5 | 85.9 | 5.2 | 91.1 |
| 66 | Cu/Cr | 20 | 167.80 | 0.75 | 21.0 | 9.0 | 30.0 |
|  |  |  |  | 1.5 | 43.9 | 7.6 | 51.6 |
|  |  |  |  | 5 | 91.5 | 7.8 | 99.3 |
| Hydrogenation under 6 MPa (60 bar) $H_2$ and 3 MPa (30 bar) CO (65° C.) | | | | | | | |
| 38 | Ru/foam | 49 | 185.67 | 0.75 | 3.8 | 5.3 | 9.1 |
|  |  |  |  | 1.5 | 4.0 | 5.3 | 9.3 |
|  |  |  |  | 5 | 4.4 | 5.4 | 9.8 |
| 85 | Cu/Cr | 20 | 153.81 | 0.75 | 16.8 | 6.3 | 23.1 |
|  |  |  |  | 1.5 | 29.4 | 6.2 | 35.6 |
|  |  |  |  | 5 | 87.1 | 6.5 | 93.6 |

Experiment B

Experiments have also been carried out to illustrate the "single step" PDO process under syngas. The experiments were again conducted in a 300 ml autoclave that was loadedwith 150 ml of a MTBE mixture, containing 685 mg $Co_2(CO)_8$, 300 mg N,N-dimethyldodecylamine and 7.00 g EO, and 10 gram hydrogenation catalyst. Then the autoclave was pressurised with syngas (4:1 $H_2$:CO) to 8 MPa (80 bar) and heated up to 75° C. The autoclave was kept at 8 MPa (80 bar) by adding syngas (2:1 $H_2$:CO). A sample was taken every 15 minutes during the first hour and every 30 minutes for the remaining time. The yields are expressed as mole % based on EO feed.

Results and Discussion B

The results of the experiments are summarised in Table 2. According to Table 2, no HPA and PDO are formed in comparative experiments that do not use $Co_2(CO)_8$ hydroformylation catalyst nor any supported metal as hydrogenation catalyst (exp. 122). The presence of $Co_2(CO)_8$ and absence of supported metal hydrogenation catalyst allows the formation of HPA with marginal production of PDO (exp. 132).

Upon addition of Cu/Zn or Cu/Cr to the $Co_2(CO)_8$-containing system PDO is formed in substantial amounts (exp. 127–128, and 120–121). Proper dosing of the amount of copper and $Co_2(CO)_8$ catalysts allows one to maximise the formation of PDO while minimising the formation of acetals (exp. 120).

By contrast other Group 11 metals such as Ag/Al or Au/Ti do not lead to significant formation of PDO (exp. 125–126).

TABLE 2

| exp. # | hydrogenation catalyst name | [g] | $Co_2(CO)_8$ [g] | EO [g] | time [h] | HPA | PDO | acetal | PDO + acetal |
|---|---|---|---|---|---|---|---|---|---|
|  |  |  |  |  |  | [mole per 100 mole EO in feed] | | | |
| no hydrogenation catalyst | | | | | | | | | |
| 122 | none | 0 | 0 | 7.20 | 0.75 | 0.0 | 0.0 | 0.0 | 0.0 |
|  |  |  |  |  | 1.5 | 0.0 | 0.0 | 0.0 | 0.0 |
| 132 | none | 0 | 0.714 | 6.97 | 0.75 | 40.5 | 1.1 | 1.9 | 3.0 |
|  |  |  |  |  | 1.5 | 31.3 | 0.3 | 2.3 | 2.7 |
| Copper catalysts | | | | | | | | | |
| 127 | Cu/Zn | 10 | 0.688 | 7.19 | 0.75 | 17.7 | 10.4 | 1.1 | 11.5 |
|  |  |  |  |  | 1.5 | 7.8 | 15.4 | 1.2 | 16.7 |
|  |  |  |  |  | 3.5 | 0.7 | 19.8 | 1.2 | 21.1 |
| 128 | Cu/Zn | 15 | 0.687 | 6.98 | 0.75 | 9.9 | 14.8 | 0.9 | 15.7 |
|  |  |  |  |  | 1.5 | 3.5 | 19.2 | 0.9 | 20.1 |
|  |  |  |  |  | 3.5 | 0.2 | 21.1 | 0.8 | 21.9 |
| 121 | Cu/Cr | 10 | 0.05 | 6.88 | 0.75 | 1.1 | 1.5 | 0.0 | 1.5 |
|  |  |  |  |  | 1.5 | 0.5 | 3.1 | 0.1 | 3.2 |
|  |  |  |  |  | 4 | 0.3 | 4.3 | 0.0 | 4.3 |
| 120 | Cu/Cr | 10 | 0.14 | 7.00 | 0.75 | 10.9 | 5.3 | 0.1 | 5.4 |
|  |  |  |  |  | 1.5 | 9.0 | 10.4 | 0.1 | 10.5 |
|  |  |  |  |  | 4 | 1.6 | 19.4 | 0.2 | 19.6 |
| Other Group 11 metal catalysts | | | | | | | | | |
| 125 | Ag/Al | 8 | 0.668 | 6.97 | 0.75 | 35.3 | 0.8 | 1.5 | 2.3 |
|  |  |  |  |  | 1.5 | 29.5 | 0.2 | 2.0 | 2.2 |
| 126 | Au/Ti | 5 | 0.686 | 7.45 | 0.75 | 41.4 | 3.9 | 0.1 | 4.0 |
|  |  |  |  |  | 1.5 | 44.3 | 1.4 | 1.9 | 3.4 |

(*) no gas renewal

What is claimed is:

1. A process for preparing a 1,3-diol by hydrogenating a feed comprising 3-hydroxyaldehyde in the presence of a catalyst and a hydrogen source wherein syngas is used as the hydrogen source and the catalyst is a heterogeneous catalyst comprising copper on a support.

2. The process of claim 1 wherein the catalyst comprises metallic copper on a support.

3. The process of claim 1 wherein the support is an inert carrier selected from the group consisting a clay, a metallic or glass sponge, an inorganic carbide, an inorganic oxide, and carbon.

4. The process of claim 1 wherein the feed comprises a 3-hydroxyaldehyde of the general formula

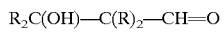

$$R_2C(OH)-C(R)_2-CH=O$$

wherein each R independently may be a hydrogen atom or may be a hydrocarbon group that is substituted or unsubstituted and aliphatic or aromatic.

5. The process of claim 1 wherein the feed comprises the product of an oxirane hydroformylation step, which product comprises a 3-hydroxyaldehyde, a solvent and a homogeneous hydroformylation catalyst.

6. The process of claim 5 wherein the homogeneous hydroformylation catalyst comprises a Co-based and/or Rh-based hydroformylation catalyst.

7. A process of preparing a 1,3-diol wherein:

a) an oxirane is hydroformylated by reaction with syngas in the presence of a homogeneous hydroformylation catalyst and a solvent, forming a 3-hydroxyaldehyde feed, and b) the 3-hydroxyaldehyde feed is hydrogenated in the presence of a heterogeneous catalyst comprising copper on a support and syngas as the hydrogen source.

8. The process of claim 7 wherein the hydroformylation step a) and the hydrogenation step b) are carried out sequentially in connected reactor vessels or in a single reactor vessel.

9. The process of claim 7 wherein the hydroformylation step a) and the hydrogenation step b) are carried out simultaneously in a single reactor vessel.

10. The process of claim 7 wherein step b) is carried out at a temperature from ambient to about 150° C. and a pressure of from atmospheric to about 15 MPa.

11. The process of claim 1 wherein the copper is present on the support in a quantity of about 0.1 to about 80% by weight, relative to the support.

12. The process of claim 11 wherein the copper is present on the support in a quantity of about 10 to about 50% by weight, relative to the support.

13. The process of claim 12 wherein the copper is present on the support in a quantity of about 25 to about 35% by weight, relative to the support.

14. The process of claim 4 wherein each group R may independently vary in size from 1 to 20 carbon atoms and may bear one or more substituents selected from the group consisting of hydroxy, alkoxy, carbonyl, carboxy, amino, cyano, cyanato, mercapto, phosphino, phosphonhyl, silyl, and halogen atoms.

15. The process of claim 14 wherein each group R may have from 1 to 10 carbon atoms.

16. The process of claim 4 wherein the 3-hydroxyaldehyde has in total from 3 to 12 carbon atoms.

17. The process of claim 16 wherein the 3-hydroxyaldehyde has in total from 3 to 8 carbon atoms.

* * * * *